US005834449A

United States Patent [19]
Thompson et al.

[11] Patent Number: 5,834,449
[45] Date of Patent: Nov. 10, 1998

[54] TREATMENT OF AORTIC AND VASCULAR ANEURYSMS WITH TETRACYCLINE COMPOUNDS

[75] Inventors: Robert W. Thompson, Chesterfield, Mo.; Lorne M. Golub, Smithtown, N.Y.

[73] Assignees: The Research Foundation of State University of New York, Albany, N.Y.; Washington University, St. Louis, Mo.

[21] Appl. No.: 662,482

[22] Filed: Jun. 13, 1996

[51] Int. Cl.$^6$ ................................................ A61K 31/65
[52] U.S. Cl. .............................................................. 514/152
[58] Field of Search ............................................. 514/152

[56] References Cited

U.S. PATENT DOCUMENTS

| | | | |
|---|---|---|---|
| 4,666,892 | 5/1987 | Golub et al. | 514/152 |
| 4,935,412 | 6/1990 | McNamara et al. | 514/152 |
| 5,223,248 | 6/1993 | McNamara et al. | 514/152 |

OTHER PUBLICATIONS

Anidjar, S. Salzmann, JL, Generic, D. Lagneau, P, Camilleri, JP, and Michel, JB, "Elastase induced experimental aneurysms in rats," *Circulation* 82:973–981 (1990).

Golub, LM, Ramamurthy, NS, McNamara, TF, Greenwald, RA, and Rifkin, BR, "Tetracyclines inhibit connective tissue breakdown: New therapeutic implications for an old family of drugs", *Crit. Rev. in Oral Biol. and Med.* 2(2):297–322 (1991).

Halpern, VJ, Liao, Nackman, GB, Gandhi, RH, Irizarry, E, Scholes, JV, Ramey, WG, and Tilson, MD, "The elastase infusion model of experimental aortic aneurysms: Synchrony of induction of endogenous proteinases with matrix destruction and inflammatory cell response," *J. Vasc. Surg.* 20:51–60 (1994).

Petrinec, D, Liao, S, Holmes, DR, Reilly, JM, Parks, WC, and Thompson, RW, "Doxycycline inhibition of aneurysmal degeneration in an elastase–induced rat model of abdominal aortic aneurysm: Preservation of aortic elastin associated with suppressed production of 92 kD gelatinase," *J. Vasc. Surg* 23:336–346 (1996).

Ryan, ME, Ramamurthy, NS, and Golub, LM, "Matrix metalloproteases and their inhibition in periodontal treatment," *Curr. Opin. Periodontol.* 3:85–96 (1996).

*Primary Examiner*—Kevin E. Weddington
*Attorney, Agent, or Firm*—Hoffmann & Baron, LLP

[57] ABSTRACT

A method for inhibiting the formation and progression of abnormal vascular dilatation and/or aneurysms. The method includes administering a tetracycline compound to a mammal in an amount which is effective against the formation or progression of aneurysm, or which is effective to induce regression of an established abnormal dilatation or aneurysm. The method is of particular advantage in the treatment of mammals having an abdominal aortic aneurysm, a relatively common, and life-threatening, condition. Further, there is provided a method for inhibiting elastolytic activity in vascular tissue, to diminish excessive proteolytic degradation of vascular elastic tissues, wherein such degradation is associated with abnormal vascular dilatation or aneurysm. Also provided is an apparatus for treating mammals suffering from an abnormal vascular dilatation and/or aneurysm.

15 Claims, 2 Drawing Sheets

TREATMENT OF AORTIC AND VASCULAR ANEURYSMS WITH TETRACYCLINE COMPOUNDS

BACKGROUND OF THE INVENTION

The invention relates to a method for treating aortic and other vascular aneurysms with tetracycline compounds. More specifically, the invention relates to the inhibition of proteolytic activity related to compromise of structural integrity in vascular tissue.

The two basic types of blood vessels, arteries and veins, can be distinguished by their structural components. Arteries and veins both have a layered structure, in which several distinct layers are arranged coaxially. In arteries the layers include an inner coat or endothelial layer (tunica intima), an internal elastic lamina, a middle coat (tunica media), and an outer coat (tunica adventitia). Like arteries, veins include an inner coat (tunica intima), a middle coat (tunica media) and an outer coat (tunica adventitia), but the layers are not as thick as in arteries, and provide much less structural rigidity. Indeed veins collapse when a vessel is cut and they are no longer supported by internal blood pressure.

Because of their greater structural strength, arteries are better adapted to withstand higher internal pressures. This feature corresponds directly to their role in carrying blood away from the heart, since the heart generates large transient pressures. Internal arterial pressures normally range between about 70 (diastolic pressure) and about 120 mm Hg (systolic pressure), but arterial structure is compliant enough to withstand higher baseline pressures for extended periods, and to accommodate higher systolic peaks as well. Venous pressures are typically in the range of about 10 mm Hg, but again somewhat higher pressures can be withstood. Because the veins transport blood back to the heart after it has been distributed to tissues, veins are exposed to fewer and less severe transient fluctuations in blood pressure.

Both arteries and veins are elastic, and are capable of limited deformation in response to pressure changes. Arteries, as mentioned above, have an extra internal elastic layer, which imparts greater elasticity to the arterial structure. The arteries within the thorax are extremely distensible due to a much higher proportion of rubbery (elastin) to stiff (collagen) fibers in their walls than is found in nonthoracic arteries. Their distensibility allows the arteries to act as a reservoir of blood during ejection of blood during the cardiac cycle. As a result, peak pressures can be lower in proximal arteries than in the distal arteries which are stiffer and not as accommodating to pulsatile blood pressure transients. However, the compliance of these vascular structures is not unlimited, and high blood pressure (hypertension) can overcome their ability to compensate, resulting in abnormal (excessive) dilatation and even causing the blood vessels to burst.

When a blood vessel is exposed to hypertension, it tends not to overdilatate along its entire length, but instead dilatates in a localized region. Typically these dilatations are produced at the region in the wall which is weakest, whether inherently or as a result of disease or trauma. As the dilatation progresses, a more pronounced widening or sac, called an aneurysm, is produced. If blood pressure remains high or goes higher, the aneurysm can burst. In the brain, ruptured blood vessels manifest as stroke, but hemorrhage from compromised vasculature can occur also in other parts of the body, leading to a life-threatening situation. Aortic aneurysms are of especial concern since, as it is the main artery leading away from the heart to the rest of the body, the aorta carries a huge volume of blood, and a rupture causes almost immediate death.

Among the causes of aneurysms are arteriosclerosis, syphilis, degenerative changes and cystic necrosis of the tunica media of vessels, trauma, bacterial infections, arteritis, and congenital deformities.

Arteriosclerotic and syphilitic aneurysms are the most common types and involve principally the thoracic and abdominal aorta. Thoracic aneurysms commonly compress and erode various structures as they expand. They may erode in to the lungs or the spinal column, through the anterior chest wall and present externally as a pulsating mass. Blood flow through aneurysms is relatively low, and as a result they become lined with clotted blood (thrombus), but this accumulation offers little structural support against the blood pressure.

Another specialized type of aneurysm is the dissecting aneurysm of the aorta, in which blood enters between, and separates, the layers of the aortic wall. Such aneurysms are typically caused by hypertension, and are accompanied by localized degenerative changes in the tissues of the vessel, potentially resulting in perforation and consequent lethal hemorrhage.

Berry aneurysms are congenital defects which occur in cerebral arteries, most commonly at the junctions of vessels in the circle of Willis. These aneurysms appear to be related to defects in the muscular coat of the vessels. Rupture is common, resulting in subarachnoid (intracranial) hemorrhage.

Of special clinical interest are aortic aneurysms, especially abdominal aortic aneurysms (AAA), which are characterized by transmural aortic wall degeneration leading to dilatation, progressive growth, and eventual rupture. Other types of aneurysms include arteriovenous fistulae, cardiac aneurysms (typically resulting from myocardial infarction), and miliary aneurysms (aneurysms in a minute artery, e.g., retinal), and the like.

While aneurysms may not be readily detected if not explicitly being looked for, they can be detected in many cases by means of characteristic clinical signs. For example, arterial aneurysm can exhibit the formation of a pulsating tumor, and often a "bruit" heard over the swelling. Pressure on contiguous parts can also be observed.

Treatment of aneurysms typically involves surgical intervention. Excision of the aneurysm, and anastomosis of the vessel may be performed, often using a replacement vessel or an artificial prosthesis. Alternatively, a supporting structure such as a stent or other intravascular device may be implanted into the vessel to relieve stress. However, surgical interventions are useful only after the aneurysm has arisen, typically not being capable of prophylactic use. Moreover, such methods are invasive, requiring surgical operation and hospitalization of the patient.

Prophylactic methods for preventing the formation of aneurysm tend to rely on reducing blood pressure, in an effort to reduce mechanical stress on the vasculature. These methods involve use of drugs which can have undesirable side effects, e.g., kidney or liver damage, especially over long term use. More important, these drugs are not indicated for improving the structure of the blood vessel or altering the cellular and molecular processes involved in abnormal dilatation. Moreover, no evidence has been found that these drugs can cause the regression of established aneurysms.

The most conspicuous histologic findings in many aneurysms, especially AAA, are the destruction of the medial elastic lamellae, chronic inflammation within the outer aortic wall, and medial neovascularization. Increased local production of connective tissue proteinases including serine proteases, plasminogen activators, and matrix metalloproteinases (MMPs) has been documented in aneurysm tissue. Any of these enzymes might contribute to the degradation of structurally important extracellular matrix proteins in aneurysms, but it has not been clear which if any specific mechanism might play a particularly important role in the progressive pathobiologic condition of AAA.

The tetracyclines are a well known and successful class of antibiotics. Compounds such as tetracycline, sporocycline, etc., are broad spectrum antibiotics, having utility against a wide variety of bacteria. The parent compound, tetracycline, has the following general structure:

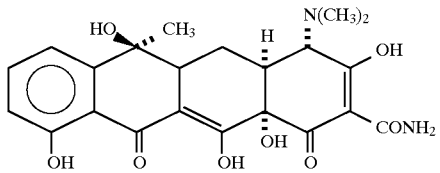

The numbering system of the multiple ring nucleus is as follows:

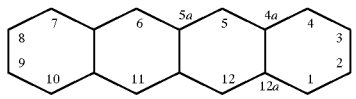

Tetracycline, as well as the 5-OH (terramycin) and 7-Cl (aureomycin) derivatives, exist in nature, and are all well known antibiotics. However, natural tetracyclines may be modified without losing their antibiotic properties, although certain elements of the structure must be retained to do so. The modifications that may and may not be made to the basic tetracycline structure have been reviewed by Mitscher (1978). According to Mitscher, the modification at positions 5–9 of the tetracycline ring system can be made without causing the complete loss of antibiotic properties. However, changes to the basic structure of the ring system, or replacement of substituents at positions 1–4 or 10–12, generally lead to synthetic tetracyclines with substantially less, or essentially no, antibacterial activity. For example, 4-dedimethylaminotetracycline is commonly considered to be a non-antibacterial tetracycline.

The use of tetracycline antibiotics, while generally effective for treating infection, can lead to undesirable side effects. For example, the long-term administration of antibiotic tetracyclines can reduce or eliminate healthy flora, such as intestinal flora, and can lead to the production of antibiotic resistant organisms or the overgrowth of yeast and fungi.

Recently, a new class of compounds has been defined which are structurally related to the antibiotic tetracyclines, but which have had their antibiotic activity substantially or completely extinguished by chemical modification. These compounds, known as chemically-modified tetracyclines (CMTs), have been found to possess a number of interesting properties, such as the inhibition of excessive collagenolytic activity in vivo. Specifically, CMTs have been shown to inhibit collagen degradation by some MMPs, a family of zinc-dependent enzymes with a broad spectrum of connective tissue substrates. See, for example, Golub et al. (1991); Ryan (1996).

In view of the above considerations, it is clear that existing methods for preventing and/or treating vascular aneurysms have undesirable limitations. Moreover, there presently is no practical method available for inducing regression of established or pre-existing aneurysms. Nor is it clear what mechanism(s) is (are) actually involved in the generation and progression of abnormal dilatations and aneurysms.

Accordingly, it is one of the purposes of this invention to overcome the above limitations in treating vascular and especially arterial aneurysms, by providing a method of preventing their formation, but without being subject to undesirable side effects or requiring intrusive or invasive interventions. It is another purpose of the invention to provide a method of inducing the regression of established aneurysms to cause the vessel to return to a safer and relatively more normal state.

SUMMARY OF THE INVENTION

It has now been discovered that these and other objectives can be achieved by the present invention, which provides a therapeutic method for inhibiting vascular aneurysm, the method including administering an anti-aneurysmal amount of a tetracycline compound to a mammal in need of anti-aneurysmal therapy, thereby inhibiting the formation or progression of an aneurysm in vascular tissue in the mammal.

The vascular tissue suitable for treatment according to the method is preferably an artery of the mammal, more preferably, the aorta and especially the abdominal aorta of the mammal.

The therapeutic method preferably employs administration of a tetracycline compound having substantially no antimicrobial activity. Also, the method can include enterally administering the tetracycline compound.

In another embodiment, the invention provides a method for inhibiting development of, or inducing regression of, an aneurysm in vascular tissue susceptible to the formation of, or exhibiting, an aneurysm, wherein the method includes contacting the vascular tissue with an inhibitor of elastolytic activity in an amount sufficient to inhibit development of, or induce regression of, an aneurysm in the vascular tissue.

The inhibitor of elastolytic activity can be a matrix metalloproteinase inhibitor, such as a gelatinase inhibitor. Such compounds include tetracycline compounds, including tetracycline compounds having antimicrobial activity as well as those having substantially no antimicrobial activity.

The method is useful for inhibiting elastolytic activity in arterial tissue, including in aortic tissue, and especially in abdominal aortic tissue.

Preferably, this embodiment involves administering the inhibitor of elastolytic activity to a mammal in an amount sufficient to inhibit development of, or induce regression of, a vessel dilatation or aneurysm in the subject.

Also provided is a medical apparatus, including an intravascularly implantable device capable of intravascular delivery of an anti-aneurysmal agent, preferably a tetracycline compound, to a site of aneurysm in a blood vessel upon implantation.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawings, wherein.

DETAILED DESCRIPTION OF THE PREFERRED EMBODIMENTS

Figure 1:
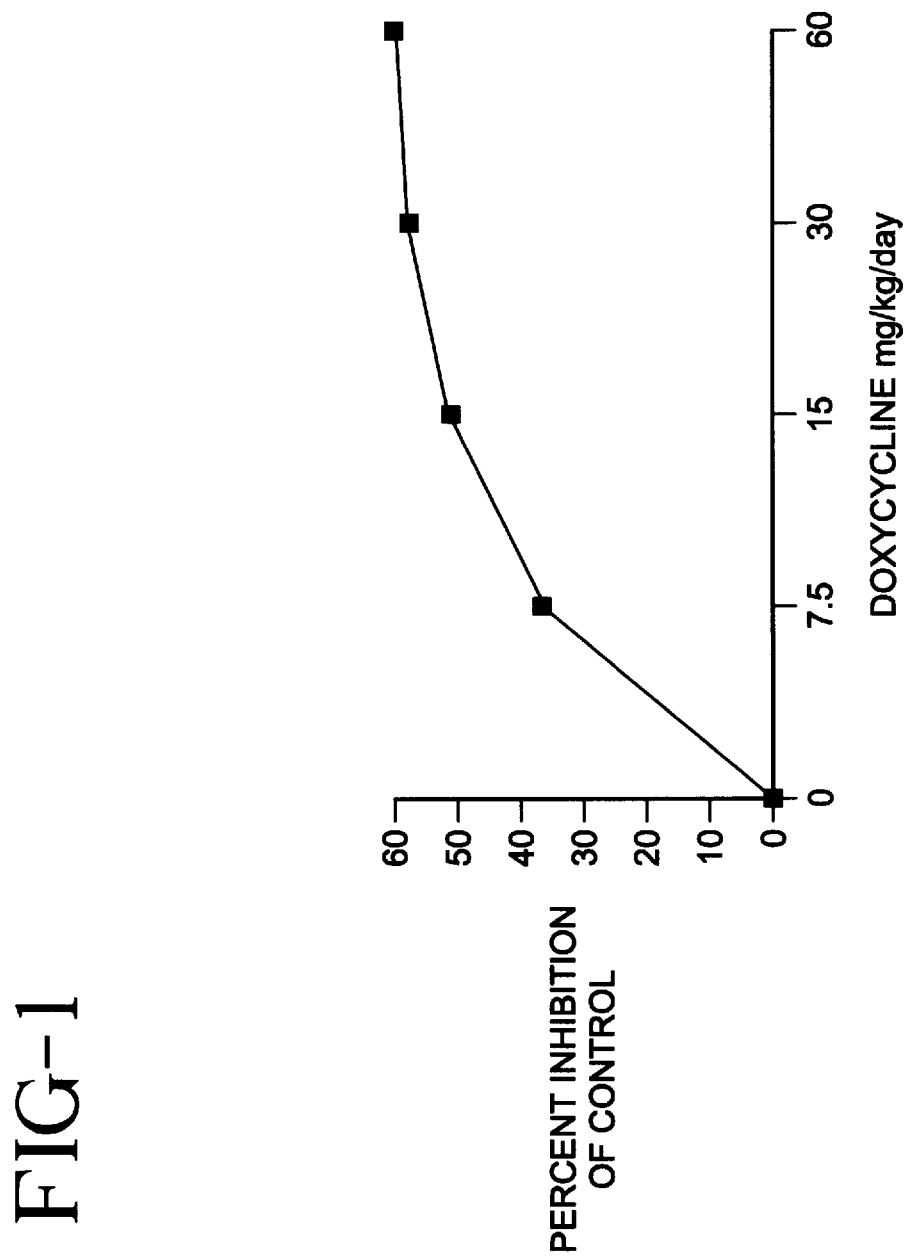
FIG. 1 is a graph illustrating the dose-dependent effect of a tetracycline compound (doxycycline) in inhibiting induced dilatation of arterial diameter.

The present invention is directed to a method of treating aneurysms in blood vessels (vascular tissue), both to prevent their inception and growth, as well as to induce regression of established aneurysms. The invention extends not only to the prophylaxis, treatment, and management of aneurysms, as that term might be conventionally understood, but also to the prophylaxis, treatment, and management of any abnormal dilatations of blood vessels. Such dilatations are often considered to be predictive of aneurysm formation, or diagnostic of incipient aneurysms, and are treatable or preventable by means of the invention. "Aneurysm," as used herein, means not only conventional vascular aneurysms, but also refers to any abnormal localized dilatations of blood vessels. Further, the method extends to the prophylaxis, treatment, and management of complications of atherosclerosis associated with aneurysms in arteries and other locations, including arterial occlusion (thrombosis), embolization, and dissection.

In one embodiment, the method of the invention involves administration of an anti-aneurysmal amount of a tetracycline compound to a subject in need of anti-aneurysmal therapy. An anti-aneurysmal amount of a tetracycline is an amount which prevents the formation of an aneurysm in a blood vessel, or which inhibits the progression or induces the regression of an established (pre-existing) aneurysm. Thus, a mammal in need of anti-aneurysmal therapy is a mammal which is vulnerable to the formation of an abnormal blood vessel dilatation or aneurysm, or a mammal which exhibits an established blood vessel dilatation or aneurysm. The method of the invention is effective in resisting the formation of such aneurysms, and is helpful in causing the regression of pre-existing aneurysms to return the involved blood vessel (aneurysmal tissue) to a safer state, preferably to a normal or near normal state.

The method of this embodiment employs any suitable tetracycline compound having an anti-aneurysmal effect. In using a tetracycline compound as the agent administered according to the invention, the observed anti-aneurysmal effect appears to be unrelated to, and independent of, any antimicrobial activity such a compound might have. Accordingly, the tetracycline may be an antimicrobial tetracycline compound, or it may be a tetracycline analogue having little or no significant antimicrobial activity. For the purposes herein a tetracycline analogue having little or no significant antimicrobial activity is referred to as a CMT.

Preferred antimicrobial tetracycline compounds (anti-aneurysmal agents) include, for example, tetracycline per se, as well as derivatives thereof. Preferred derivatives include, for example, aureomycin and chloromycin.

If a CMT is to be employed, it is preferred that the CMT lack the dimethylamino group at position 4 of the ring structure of tetracycline. Such chemically-modified tetracyclines include, for example, 4-dedimethylaminotetracycline (CMT-1), 4-dedimethylamino-5-oxytetracycline, 4-dedimethylamino-7-chlorotetracycline (CMT-4), 4-hydroxy-4-dedimethylaminotetracycline (CMT-6), 5 a,6-anhydro-4-hydroxy-4-dedimethylaminotetracycline, 6-demethyl-6-deoxy-4-dedimethylaminotetracycline (CMT-3), 4-dedimethylamino-12a-deoxytetracycline (CMT-7), and 6-$\alpha$-deoxy-5-hydroxy-4-dedimethylaminotetracycline (CMT-8). Also, tetracyclines modified at the 2 carbon position to produce a nitrile, e.g., tetracyclinonitrile, are useful as non-antibacterial, anti-metalloproteinase agents.

Further examples of tetracyclines modified for reduced antimicrobial activity include 6-$\alpha$-benzylthiomethylenetetracycline, the mono-N-alkylated amide of tetracycline, 6-fluoro-6-demethyltetracycline, and 11$\alpha$-chlorotetracycline.

Among the advantages of the present invention is that a tetracycline compound can be administered in an amount which has substantially no antibacterial activity, but which is effective for reducing pathology, or for inhibiting the undesirable consequences, associated with aneurysms in blood vessels. Thus, antibacterial tetracyclines can be used in amounts which are effectively non-antimicrobial. Alternatively, as noted above, the tetracycline compound can have been modified chemically to reduce or eliminate its antimicrobial properties. The use of such modified tetracyclines is preferred in the present invention since they can be used at higher levels than antimicrobial tetracyclines, while avoiding certain disadvantages, such as the indiscriminate killing of beneficial microbes which often accompanies the use of antimicrobial or antibacterial amounts of such compounds.

Inter alia, the invention provides a method for protecting elastic fibers in the medial lamellae of blood vessels from abnormal degradation which can otherwise lead to dilatation and/or aneurysm. Accordingly, the method involves selectively inhibiting elastolytic activity in the vascular tissue. Elastolytic activity includes protease-associated structural deterioration of arterial elastin and associated materials, such as extracellular matrix components. It appears that elastolytic activity can increase following insult or trauma to a blood vessel, and that this phenomenon is associated with dilatation of the vessel. Accordingly, in this embodiment, the invention encompasses the selective inhibition of such abnormal or elevated elastolytic activity in the vascular tissue.

In this embodiment, the method involves contacting vascular tissue with an inhibitor of elastolytic activity in an amount (an anti-elastolytic amount) sufficient to selectively inhibit elastolytic activity in the tissue. The method can be performed in vitro, as in experimental or diagnostic inhibition of elastolytic activity in isolated specimens of vascular tissue, or in vivo, wherein a living mammalian subject is treated to reduce elastolytic activity in a vascular tissue in which such activity might cause abnormal vessel dilatation or aneurysm.

The inhibition of elastolytic activity is preferably selectively directed against proteolytic activity associated with tissue matrix metalloproteases. Among other anti-metalloprotease effects, the invention is effective to accomplish the selective inhibition of gelatinase, i.e., MMP-9 (92 kD gelatinase). Thus, in general, inhibitors of matrix metalloproteases (including collagenases, etc.), and more specifically inhibitors of gelatinase, are capable of use according to the method of the invention.

Other inhibitors of MMP activity are also suitable for use in inhibiting abnormal vascular dilatations and aneurysms.

Suitable inhibitors include, for example, endogenous inhibitors, such as tissue inhibitors of MMPs (TIMPs) and α-macroglobulins, and synthetic inhibitors, such as chelating agents (e.g., EDTA and 1,10-phenanthroline), peptides, antibodies, and the like. Other suitable inhibitors are known, e.g., Ryan et al. (1996). Thus, the invention further provides a method of inhibiting MMP-related activity in vascular tissue in which such activity is considered to be excessive. Effective anti-aneurysmal inhibition of proteolytic activity can be accomplished by inhibiting the synthesis or expression of involved MMPs, or can by accomplished by inhibiting the proteolytic activity of an expressed MMP.

The maximal dosage of the active agent for a mammal is the highest dosage that is effectively anti-aneurysmal, and that does not cause undesirable or intolerable side effects. For example, a tetracycline compound can be administered in an amount of from about 0.1 mg/kg/day to about 30 mg/kg/day, and preferably from about 1 mg/kg/day to about 18 mg/kg/day. For the purpose of the present invention, side effects include clinically significant antimicrobial or antibacterial activity, as well as toxic effects. For example, a dose in excess of about 50 mg/kg/day would likely produce side effects in most mammals, including humans. In any event, the practitioner is guided by skill and knowledge in the field, and the present invention includes without limitation dosages which are effective to achieve the described phenomena.

The agents useful according to the method of the invention exhibit their beneficial effect in a dose-dependent manner. For example, within broad limits, administration of larger quantities of a tetracycline compound will induce a larger or stronger response than will administration of a smaller amount. Moreover, anti-aneurysmal efficacy has been observed at dosages below the level at which toxicity is seen.

A tetracycline compound can be administered to a subject by any available and effective route, including enteral and parenteral routes. Oral administration is a preferred mode of administration. Injection of the agent, e.g., intravenous, intraarterial, intramuscular, subcutaneous, etc., can also be employed as determined by the skilled artisan.

A preferred pharmaceutical composition for use in the method of the invention comprises a tetracycline compound in a suitable pharmaceutical carrier or excipient as understood by practitioners in the art. The compositions are formulated with carriers suitable for administration orally, topically, by injection, or by other means. Time-release or controlled-delivery administration can be employed according to known methods. The means of delivery of the tetracycline compound with the pharmaceutical carrier can be in the form of a capsule, compressed tablet, pill, solution, or suspension suitable for oral administration to the subject.

The chemical and physical characteristics of the agent can influence the efficiency of particular modes of administration. For example, a more lipophilic tetracycline compound could produce better blood levels by oral administration, but lower blood levels by subcutaneous injection, whereas another agent might have properties predisposing it to be more effectively delivered by vascular perfusion. The skilled artisan will understand how to effectively deal with such considerations as needed in the particular case.

The conditions treatable by means of the present invention occur in mammalian subjects. Human patients are by far the most important subjects treatable according to the method of the invention, but the method can be practiced for the benefit of other mammals, including, for example, pet animals such as dogs and cats, laboratory animals such as rats and mice, as well as farm animals such as horses and cows.

The method of the invention can be implemented by directed delivery of the tetracycline compound or other inhibitory compound to the site of the incipient or existing vessel dilatation or aneurysm. In one embodiment, the invention involves the use of medical apparatus, such as an intravascularly implantable device, which enables intravascular delivery of the active agent. Implantable devices suitable for use include devices such as stents, catheters, embolic coils, filters, cannulas, prostheses, and other such devices known in the art. The active agent can be included by coating onto a surface of the device, or if the device is made of polymeric material, the agent can be incorporated into the material for release into the surrounding tissue when implanted. Alternatively, the coating may include a polymeric material such as a water-soluble polymer, so that the active agent can be delivered in situ in a controlled release fashion. Polymers suitable for use in these methods are well known in the art, and include polymers such as cellulosic polymers, polyacrylates and polyacrylamides, polyvinyl alcohols, polyvinylpyrrolidone, and other hydrophilic polymers. Alternatively, polymers have porosity suited to release of the active agent into the surrounding tissues of fluids can be employed. In addition, catheters can be used to directly infuse or perfuse the agent into the blood vessel for controlled and localized or systemic delivery of the agent. A preferred mode of delivery the agent is to employ a stent with a coating of material for releasing the agent directly into the blood vessel wall at the site of implantation, while also providing direct structural support for the vessel at that site. Alternatively, a dual balloon perfusion catheter is used to isolate the site of dilatation or aneurysm, and the tetracycline compound or other protease inhibitor can be delivered to the isolated area without involvement of surrounding tissues.

Tetracycline compounds suitable for use according to the invention are commercially available or can be prepared by methods known in the art. Some suitable methods include those described by Mitscher (1978).

The following examples are provided to assist in a further understanding of the invention. The particular materials and conditions employed are intended to be further illustrative of the invention and are not limiting upon the reasonable scope thereof

EXAMPLE 1

Male Wistar rats (350–400 g) were subjected to perfusion of an isolated segment of the infrarenal abdominal aorta with 50 units of porcine pancreatic elastase, using the method described by Anidjar et al. (1990); Halpern et al. (1994); and Petrinec (1996). This method is an accepted model for experimental induction of abdominal aortic aneurysms (AAA). The animals (n=6 rats in each group) were then treated with twice-daily subcutaneous injections of either saline vehicle (control), or various doses of doxycycline (Dox) or one of four different, non-antibiotic, chemically-modified tetracyclines (CMTs; CollaGenex, Inc., Newtown, Pa.). Aortic diameter (AD) was measured with microcalipers before and after elastase perfusion, and just prior to sacrifice on day 7. AAA were defined as an increase in final AD to at least twice that measured before perfusion ($\geq 100\%$ increase). Aortic tissues from two animals in each group were perfusion-fixed with 10% neutral buffered formalin, embedded in paraffin, and stained with Verhoeff-van Geisen (VVG) for elastin. Tissues from the remaining animals were extracted, normalized to total protein, and analyzed by gelatin substrate zymography as described (Thompson et al. 1995; Halpern et al. 1994; Petrinec 1996).

Figure 2:
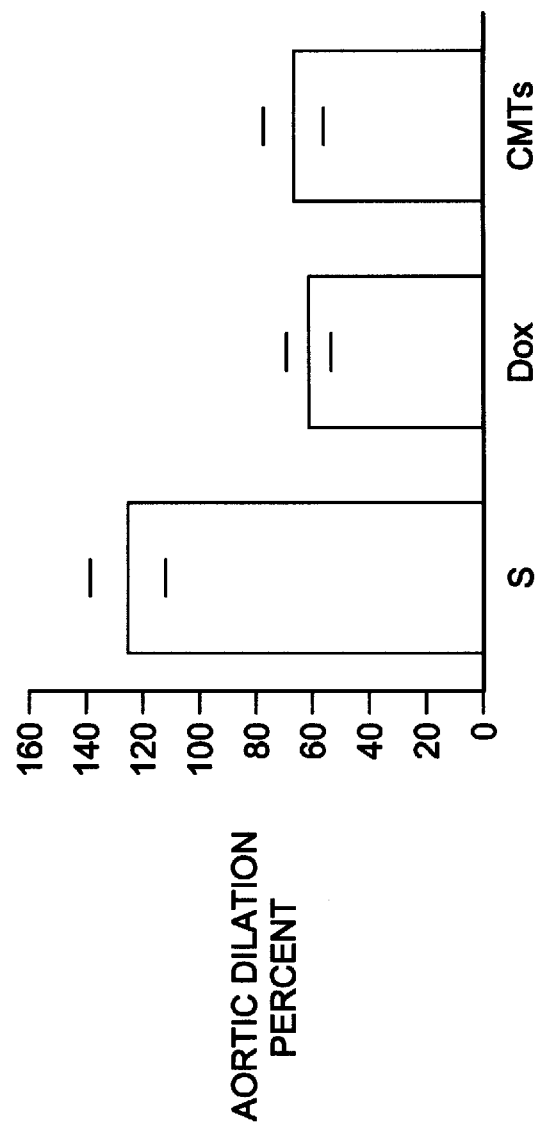
FIG. 2 is a histogram chart comparing the effects on mean arterial diameter of saline, doxycycline, and a group of chemically-modified tetracycline compounds having substantially no antimicrobial activity.

For saline-treated control animals, mean AD increased by 125±18%, and 5 of the 6 (83%) of the animals had AAA as defined. Rats treated with 60 mg/kg/day Dox had significantly less aortic dilatation (mean 61±7%) than the control animals, and no AAA were observed (p<0.01). The effects of Dox were dose-dependent, with maximal inhibition at about 12.5 mg/kg/day. FIG. 1 shows the dose-dependent inhibition of aortic dilatation by Dox, where the data indicate the percent inhibition of aortic dilatation for the Dox-treated rats compared to the saline-treated controls (S) (p<0.01, Student's t-test vs. S). At 15 mg/kg/day, the CMTs similarly inhibited aortic dilatation induced by elastase perfusion. FIG. 2 shows the inhibition of aortic dilatation by the CMTs as a pooled group, where the data indicate the degree of aortic dilatation observed in S-, Dox- or CMT-treated animals (p<0.05, Student's t-test vs. S). This was statistically significant for CMT-3, CMT-7, and CMT-8 (p<0.05); whereas, while CMT-4 also inhibited aortic dilatation, its effect did not reach statistical significance in this study. Compared to Dox at the same dose, the relative efficacies of the CMTs in suppressing aneurysmal dilatation were as follows: 92% (CMT-3); 75% (CMT-4); 92% (CMT-7); and 105% (CMT-8). VVG-stained aortic sections revealed substantial degradation of the medial elastic lamellae in all saline-treated controls, associated with mononuclear inflammation. The tetracycline compounds consistently prevented aortic elastin degradation without altering the inflammatory response. Aortic extracts from control animals exhibited a marked increase in production of MMP-9 by gelatin zymography, but this was substantially diminished in tetracycline-treated rats.

Accordingly, tetracycline derivatives inhibit aortic dilatation and elastin degradation in the elastase-perfused rat aorta. The tetracycline compounds also decrease elastolytic activity associated with the increased production of elastolytic gelatinase characteristic of dilatated and aneurysmal vascular tissue. This observed effect of the tetracycline compounds appears to be independent of the inflammatory response in affected tissues. Pharmacologic inhibition of such elastolytic activity can thereby be employed as a novel therapeutic strategy by which to suppress ongoing aortic wall matrix destruction and to limit the progressive growth of AAA. Indeed, the regression of AAA and aortic dilatation can be effected by inhibition of MMPs according to the invention.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

BIBLIOGRAPHY

Anidjar, S, Salzmann, J L, Generic, D, Lagneau, P, Camilleri, J P, and Michel, J B, "Elastase induced experimental aneurysms in rats," *Circulation* 82:973–981 (1990).

Golub, L M, Ramamurthy, N S, McNamara, T F, Greenwald, R A, and Rifkin, B R, "Tetracyclines inhibit connective tissue breakdown: New therapeutic implications for an old family of drugs", *Crit. Rev. in Oral Biol. and Med.* 2(2):297–322 (1991).

Halpern, V J, Liao, Nackman, G B, Gandhi, R H, Irizarry, E, Scholes, J V, Ramey, W G, and Tilson, M D, "The elastase infusion model of experimental aortic aneurysms: Synchrony of induction of endogenous proteinases with matrix destruction and inflammatory cell response," *J. Vasc. Surg.* 20:51–60 (1994).

Mitscher, L A, *The Chemistry of the Tetracycline Antibiotics*, Ch. 6, Marcel Dekker, New York (1978).

Petrinec, D, Liao, S, Holmes, D R, Reilly, J M, Parks, W C, and Thompson, R W, "Doxycycline inhibition of aneurysmal degeneration in an elastase-induced rat model of abdominal aortic aneurysm: Preservation of aortic elastin associated with suppressed production of 92 kD gelatinase," *J. Vasc. Surg* 23:336–346 (1996).

Ryan, M E, Ramamurthy, N S, and Golub, L M, "Matrix metalloproteases and their inhibition in periodontal treatment," *Curr. Opin. Periodontol.* 3:85–96 (1996).

What is claimed is:

1. A method for inhibiting vascular aneurysm, comprising administering an anti-aneurysmal amount of a tetracycline compound to a mammal in need of anti-aneurysmal therapy, thereby inhibiting the development of, or inducing the regression of, an aneurysm in vascular tissue in said mammal.

2. A method according to claim 1, wherein said vascular tissue is an artery of said mammal.

3. A method according to claim 1, wherein said vascular tissue is the aorta of said mammal.

4. A method according to claim 1, wherein said vascular tissue is the abdominal aorta of said mammal.

5. A method according to claim 1, wherein said tetracycline compound has substantially no antimicrobial activity.

6. A method according to claim 1, wherein said administering comprises enterally administering said tetracycline compound.

7. A method for inhibiting development of, or inducing regression of, an aneurysm in vascular tissue susceptible to the formation of, or exhibiting, an aneurysm, comprising contacting said vascular tissue with an inhibitor of elastolytic activity in an amount sufficient to inhibit development of, or induce regression of, an aneurysm in said vascular tissue.

8. A method according to claim 7, wherein said inhibitor of elastolytic activity is a matrix metalloproteinase inhibitor.

9. A method according to claim 7, wherein said inhibitor of elastolytic activity is a gelatinase inhibitor.

10. A method according to claim 7, wherein said inhibitor of elastolytic activity comprises a tetracycline compound.

11. A method according to claim 10, wherein said tetracycline compound has substantially no antimicrobial activity.

12. A method according to claim 7, wherein said vascular tissue is arterial tissue.

13. A method according to claim 7, wherein said vascular tissue is aortic tissue.

14. A method according to claim 7, wherein said vascular tissue is abdominal aortic tissue.

15. A method according to claim 7, wherein said method comprises administering said inhibitor of elastolytic activity to a mammal in an amount sufficient to inhibit development of, or induce regression of, an aneurysm in said mammal.

* * * * *

UNITED STATES PATENT AND TRADEMARK OFFICE
CERTIFICATE OF CORRECTION

PATENT NO. : 5,834,449
DATED : November 10, 1998
INVENTOR(S) : Thompson, et al

It is certified that error appears in the above-identified patent and that said Letters Patent is hereby corrected as shown below: Column 1, line 4, please insert --This invention was made with the Government support under Grant No. R37 DE-03987 awarded by the National Institutes of Health through the National Institute of Dental Research and Grant No. HL 29594 awarded by the National Institutes of Health. The Government has certain rights in the invention. Support was also provided under Grant No. 95090860 awarded by the American Heart Association and a Faculty Fellowship awarded by the American College of Surgeons. --;

<u>In Column 8, Line 46,</u>   the patent now reads "thereof"; should read --there of. --.

Signed and Sealed this

Twenty-eighth Day of March, 2000

Attest:

Q. TODD DICKINSON

*Attesting Officer*   *Commissioner of Patents and Trademarks*